June 23, 1936. V. S. HILLOCK Plant Pat. 185
ROSE
Filed Feb. 8, 1936
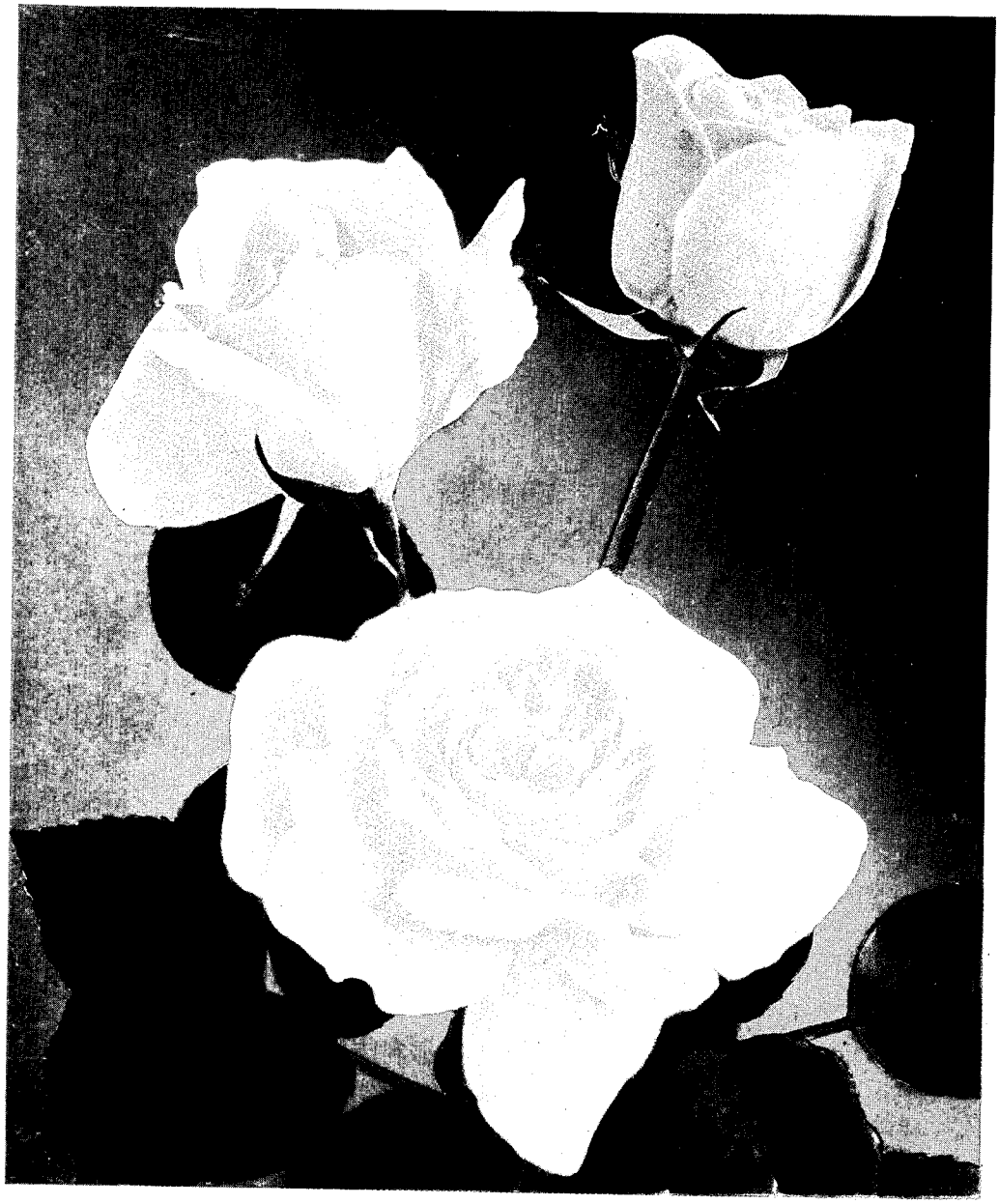
Inventor
Verne Stone Hillock
By Orville M. Kile
Plant Patent Agent Patented June 23, 1936

UNITED STATES PATENT OFFICE

185

ROSE

Verne Stone Hillock, Arlington, Tex.

Application February 8, 1936, Serial No. 62,995

1 Claim. (Cl. 47—61)

This new variety is of the hybrid tea class and is the result of cross breeding carried on by myself over a period of years. The seed parent was "Golden Dawn" and the pollen parent an unnamed seedling which was in turn produced by crossing "Golden Dawn" and an un-named seedling. I have reproduced this new variety in considerable numbers through five bud-generations and have thoroughly established its permanence and novelty. This variety has not yet been offered to the public.

The accompanying illustration shows in full color and approximately full size, in the original, two buds in opening stages and a blossom in its prime. The following description is based on observations made at Arlington, Texas, over a period of years. Except where otherwise noted, observations relate to buds and blossoms of the first burst in springtime. The color references are to Ridgway's Color Standards and Nomenclature wherever plate numbers are attached.

*The plant*

*Form.*—Bush.

*Growth.*—Vigorous. Compact.

Foliage:

*Leaflets.*—Usually five, occasionally seven.

*Size.*—Medium to large; more often large.

*Quantity.*—Very abundant.

*Color.*—New foliage: Upper side, red mottled with green. Under side, red. Old foliage: Upper side, dark green. Under side, normal green. Note: As the foliage gains maturity and passes from red to green, the color of the midribs and serrations change more slowly, the semi-matured foliage often becoming distinctly green while the midribs and serrations as yet remain distinctly reddish brown.

*Shape.*—Oval pointed.

*Texture.*—Upper side leathery and glossy. Under side smooth. Ribs and veins slightly more prominent than usual.

*Edge.*—Serrated.

*Serration.*—Single.

*Leaf stem.*—On new foliage, red. On old foliage, green. No prickles on foliage or leaf stems except in very rare instances.

*Stipules.*—Long and broad.

*Disease resistance.*—Extremity resistant to mildew and blackspot.

*Wood.*—New wood: Color red. Bark, smooth. Old wood: Color, green until frost, becoming almost purple after being frosted. Bark, smooth.

Thorns:

*Quantity.*—On main stalks from base, few. On laterals from stalks, few.

*Form.*—Long. Narrow base. Hooked slightly downward.

*Color when young.*—Red.

*Color when old.*—Brown.

*Position.*—Irregular. (An occasional stem is thornless.)

*Prickles.*—None.

*Short needles.*—None.

The plant of this variety may well be described as a counterpart of the plant of Golden Dawn, plus a somewhat greater volume of foliage, plus an added ability to produce long, strong, sturdy stems from high in the plant.

As is well known, Golden Dawn habitually produces long, sturdy stems from the base of the plant, its upper stems being of markedly lesser length and strength. Throughout the season this new variety duplicates the performance of Golden Dawn with reference to growth from the base and surpasses the performance of Golden Dawn with reference to length and strength of stems produced high in the plant; then in late autumn produces from high in the plant long, strong, sturdy stems such as Golden Dawn produces only from the base, each such astounding stem being topped by an enormous blossom, the diameter of such stems often being greater than the diameter of the growth from which they spring.

In this characteristic, such growth from high in the plant, this variety is unique and abnormal in high degree.

A maturing stem of this variety produces new growth from the terminal eyes, as with most hybrid-teas, and in addition, concurrent growth from other eyes along the stem, thus giving, not only high productivity, but also growth in two directions, giving to the plant both breadth and height, plus compactness. All stems are well clothed with large foliage, the foliage volume being such that the canes of the compact plant are habitually obscured throughout the season. The foliage appears to be a counterpart of the distinctive foliage of Golden Dawn, produced in full or even greater volume.

*The flower*

*Blooming habit.*—This rose tends to bloom in monthly bursts as is the habit of pure hybrid-teas, but the duration of the bursts is such that they habitually overlap and an established bush is seldom out of bloom throughout the summer except in August.

Bud:

*Size.*—Large to very large.

*Form.*—Ovoid—so slightly ovoid that it becomes pointed with the first slight movement of the petals in opening.

*Weather effects.*—Not affected by wet weather. Not affected by heat, except that it will burn in extreme heat as any rose will do. It is, however, extremely resistant to destruction by heat.

*Color.*—When the sepals first divide—before recurving—the rose appears to be red. But as the sepals recurve and the petals begin to unfurl, the bud is disclosed as a deep Rose Pink (Plate XII) on the reverse, usually carrying markings varying from deep salmon to carmine and of varying extent and depth. The base of each petal is aproximately Apricot Yellow (Plate IV). The inner surface of the petals is popularly described as pearl pink in spring, silvery pink in late autumn. The former is approximately La France Pink (Plate I).

*Sepals.*—The sepals are serrated. Some of of them extend above the bud and are branched. Other sepals are shorter, do not extend above the bud, and are not branched. Sepals turn back as the bud unfurls.

*Calyx.*—Funnel-shaped. Remarkably small for the size of the blossom. Smooth.

*Peduncle.*—Very long. Slightly prickly. Sometimes red; sometimes green; sometimes red on one side and green on the other. Very strong, stiff and erect.

*Opening.*—The bud opens well in all weathers.

Bloom:

*Size.*—Large to very large. Usually five to six inches across when fully expanded, in late autumn sometimes more than six.

*Borne.*—The rose is habitually borne singly except that in very late autumn an occasional spray appears.

*Stems.*—Long to very long. Strong to very strong.

*Form.*—Cupped, which form is retained to the end.

*Petalage.*—Double. Forty to sixty petals. When fully expanded, the center is habitually exposed.

*Color.*—(See bud.) While the general color tone of the opened flower is lighter than that of the bud, throughout the life of the flower the inner surface of the petals is pearl pink to silver pink according to the season. The reverse of the petals throughout the life of the flower retains most of its deep rose pink. However the salmon tones become much more prominent on the more visible portions of the petals, thus giving the lighter color tone to the opened flower. The base of each petal retains its yellow, fading slightly to Buff-Yellow (Plate IV). A peculiar shell-like brilliancy enlivens all colors. The color is held well throughout the lifetime of the bloom.

Petals:

*Texture.*—Of average thickness. Soft to the touch.

*Appearance.*—Smooth on both surfaces. Lightly veined.

*Form.*—Oval. Scalloped.

*Arrangement.*—Imbricated (usually without petaloids).

*Persistence.*—Drop off cleanly.

*Fragrance.*—Strong tea fragrance.

*Lasting quality.*—The blossom is longlasting either on the plant or as a cut flower.

Genital organs:

*Stamens—anthers.*—Larger than average hybrid-tea. Color, brown and yellow; arrangement, regular around styles.

*Stamens—filaments.*—Medium to long, uneven in length; color, usually yellow, sometimes pink and yellow.

*Pollen.*—Yellow.

*Styles.*—Bunched; uneven length; short to medium; many.

*Stigmas.*—Yellow.

*Ovaries.*—Usually all tightly enclosed; occasionally a few protrude.

Fruit: The variety is fertile with its own pollen.

*Form.*—Flat-headed. Occasionally seed protrude though seldom.

*Aspect.*—Smooth. The fruit appears to be a counterpart of the fruit of Golden Dawn but is produced with greater frequency.

*Color at maturity.*—Brownish-yellow.

*Sepals.*—Permanent. Recurved.

*Comparison*

I know of no pink rose to which the blossom of this variety can be compared with informative intent. Thousands of visitors have viewed this variety in my field, including some of the most highly informed amateur and professional rosarians on this continent. No visitor has at any time offered a comparison of this rose to any other pink rose.

The only informative comparison offered, or known to me, lies in the similarity of the bud and blossom of this variety to the bud and blossom of Golden Dawn, with wide color differences explained.

However, another point of difference arises in such comparison. The bud of Golden Dawn, having attained full development, habitually opens quickly into a fully expanded blossom. On the other hand, the bud of this variety, having attained full development, opens with marked slowness, having excellent form at each and every stage of development.

Having thus disclosed my invention, I claim:

The variety of hybrid tea rose plant herein shown and described, characterized particularly by its unusual prolificacy in the production of fall flowering shoots, by its foliage with reddish edgings, and markings, and by its large well-formed flowers of distinctive coloration and other desirable qualities as described.

VERNE STONE HILLOCK.